(12) United States Patent
Shobayashi

(10) Patent No.: US 9,078,776 B2
(45) Date of Patent: Jul. 14, 2015

(54) HIGHLY FLEXIBLE STENT WITH SINUSOIDAL PATTERN

(71) Applicant: World Medish Co., Ltd, Tokyo (JP)

(72) Inventor: Yasuhiro Shobayashi, Tokyo (JP)

(73) Assignee: Biomedical Solutions Inc., Tokyo (JP)

( * ) Notice: Subject to any disclaimer, the term of this patent is extended or adjusted under 35 U.S.C. 154(b) by 0 days.

(21) Appl. No.: 14/185,292

(22) Filed: Feb. 20, 2014

(65) Prior Publication Data

US 2015/0005871 A1 Jan. 1, 2015

(30) Foreign Application Priority Data

Jun. 28, 2013 (JP) .................................. 2013-137130

(51) Int. Cl.
*A61F 2/88* (2006.01)
*A61F 2/90* (2013.01)
(52) U.S. Cl.
CPC .... *A61F 2/88* (2013.01); *A61F 2/90* (2013.01)
(58) Field of Classification Search
CPC ....................................................... A61F 2/915
See application file for complete search history.

(56) References Cited

U.S. PATENT DOCUMENTS

| 2007/0225789 | A1  | 9/2007 | Kavanagh et al. |
| 2011/0230957 | A1* | 9/2011 | Bonsignore et al. ......... 623/1.16 |
| 2012/0078341 | A1  | 3/2012 | Kao |
| 2012/0172972 | A1  | 7/2012 | Meyer et al. |

FOREIGN PATENT DOCUMENTS

| JP | 2003-93518 A | 4/2003 |
| JP | 2003/93519 A | 4/2003 |
| JP | 2010/264261 A | 11/2010 |
| JP | 2010-535075 A | 11/2010 |
| WO | WO 2010/090348 A1 | 8/2010 |
| WO | WO 2011/056981 A2 | 5/2011 |

OTHER PUBLICATIONS

Sepehr Sani, et al., "Treatment of wide-necked cerebral aneurysms with the Neuroform2 Treo stent. A prospective 6-month study", Neurosurg. Focus , vol. 18, pp. 1-5 (Feb. 2005).

(Continued)

*Primary Examiner* — Thomas J Sweet
*Assistant Examiner* — Wade P Schutte
(74) *Attorney, Agent, or Firm* — Muncy, Geissler, Olds & Lowe, P.C.

(57) ABSTRACT

A stent has circular bodies having a wavy-line pattern and arranged side-by-side and coiled elements 15 arranged between the circular bodies that are adjacent and extending in a spiral manner, and apices on opposite sides of the wavy-line pattern of the circular bodies that are adjacent are connected by way of the coiled elements 15. A knob portion 19 is formed at each apex of the wavy-line pattern, and the knob portion 19 includes an extension portion 19a extending in the axis direction and a semicircle portion 19b formed at a tip of the extension portion, and the coiled element 15 is connected with the knob portion 19. A slit is formed at a part of the extension portion 19a of the knob portion 19, and the slit 21 extends in the axis direction from an inner peripheral portion at the apex of the wavy-line pattern of the circular body.

5 Claims, 13 Drawing Sheets

(56) References Cited

OTHER PUBLICATIONS

Randall T. Higashida, et al., "Initial Clinical Experience with a New Self-Expanding Nitinol Stent for the Treatment of Intracranial Cerebral Aneurysms: The Cordis Enterprise Stent", AJNR Am J Neuroradiol 26, , pp. 1751-1756 (Aug. 2005).

Henkes H, et al., "A novel microcatheter-delivered, highly-flexible and fully-retrievable stent, specifically designed for intracranial use. Technical note.", Interventional Neuroradiology 9, pp. 391-393 (2003).

* cited by examiner

HIGHLY FLEXIBLE STENT WITH SINUSOIDAL PATTERN

This application is based on and claims the benefit of priority from Japanese Patent Application No. 2013-137130, filed on 28 Jun. 2013, the content of which is incorporated herein by reference.

BACKGROUND OF THE INVENTION

1. Field of the Invention

The present invention relates to a highly flexible stent placed in a luminal structure of a living body in order to expand lumen.

2. Related Art

In a biological organ having a luminal structure such as blood vessels, the trachea and the intestines, when stenosis occurs therein, a cylinder-shaped stent with mesh pattern is used in order to secure patency at a site of pathology by expanding an inner cavity at a narrowed part. These biological organs often have bent or tapered structures locally (i.e. a tubular structure of which sectional diameters of the inner cavity differ locally in an axial direction). Therefore, a stent having higher conformability has been desired which can flexibly adapt to such a complex vessel structure. Furthermore, in recent years, stents have come to also be employed for the treatment of cerebral blood vessels. Among tubular organs in a living body, the cerebral vessel system has a more complex structure. The cerebral vessel system has many bent sites and sites having tapered structures. Therefore, stents with particularly higher conformability have been required therein.

For the purpose of realizing a stent with higher conformability, the two kinds of mechanical flexibilities of a longitudinal axis direction (in a central axis direction) and a radial direction (a direction perpendicular to the longitudinal direction) of the stent are said to be important. Thereamong, the flexibility in a longitudinal axis direction refers to stiffness with respect to bending along a longitudinal axis direction or the ease of bending. The flexibility in a radial direction refers to stiffness with respect to expansion and contraction along a direction perpendicular to a longitudinal axis direction or the ease of expansion and contraction. The mechanical flexibility in a longitudinal axis direction is a property that is necessary for a stent to be flexibly bent along a longitudinal axis direction to allow adapting to a bent site of a tubular organ in a body. The mechanical flexibility in a radial direction is a property that is necessary for making the radius of a stent flexibly differ following the shape of an outer wall of a luminal structure of a tubular organ in a body so that the stent is in tight contact with the outer wall of the luminal structure. More specifically, regarding the latter, the flexibility in the radial direction, with consideration of not only a stent having lower stiffness, but also the stent being placed in an organ in a body having a tapered structure, it is necessary for a stent to have a property whereby the expansive force of the stent does not change greatly depending on local changes in sectional diameters of the inner cavity at a site having a tapered structure.

In addition, for the stent treatment of a tubular organ of a narrow and complicated structure such as cerebral blood vessels, a stent has been desired which has a superior diameter reduction property, deliverability, and expansion so that the stent can be delivered through a network of a fine tubular organ and expanded properly at a site of pathology. Normally, an endovascular stent is reduced radially (crimped) from a state of being expanded and delivered in a catheter of small diameter that is inserted to a site of pathology in a state of being radially reduced. Then, the endovascular stent is extruded by an extruder such as a pusher from the catheter and expanded at the site of pathology. While the ratio of diameter reduction for a stent employed for conventional stent treatment of carotid arteries and crural arteries is 1/6, the ratio of diameter reduction for the treatment of cerebral blood vessels must be equal, at lowest, to or less than 1/10. For example, a vessel diameter for which the stent treatment for the intracranial circulation is employed is approximately 2.5 mm to 3.5 mm. There may be a case in which a catheter of large diameter cannot be adapted for the stent treatment due to access being limited. Furthermore, as the diameter of a catheter becomes larger, the stiffness thereof becomes greater, a result of which there is a risk of the catheter causing excessive deformation or load on vessels during the delivery of the stent. If the catheter cannot accommodate a stent of small diameter, it is necessary to user a catheter of larger diameter. For this reason, in a case of employing a stent, specifically for the treatment of cerebral blood vessels, it is necessary to employ a stent which is radially reduced (crimped) and can be accommodated in a small catheter of equal to or less than 1 mm. On the other hand, in a case of a stent for cerebral blood vessels, since it is designed such that a radial force is inherently low, a stent having an outer diameter of 1 to 2 mm greater than a vascular diameter is normally employed taking consideration of the contact between the stent and the inner wall of a blood vessel weakening. Therefore, when considering application of a stent to the treatment of an intracranial blood vessel, a stent having a high diameter reduction ratio is required. Furthermore, in the stent treatment for cerebral blood vessels, it is necessary to deliver a stent that is reduced radially to a site of pathology through a lumen of a catheter placed in a tiny and tortuous blood vessel, and thus the stent is required to pass through the lumen of a tortuous catheter. Therefore, a stent has been desired which has higher deliverability, which is arrived at by securing flexibility in a state of being reduced radially. Moreover, in order to extrude and expand a stent from a catheter at a desired site of pathology by a pusher, it has been desired such that an extrusion force can be transmitted to the stent efficiently in a longitudinal axis direction.

SUMMARY OF THE INVENTION

The structures of a stent are generally classified into the two types of open cell structures and closed cell structures. Since a stent having an open cell structure (refer to Sepehr Sani, et al., "Treatment of wide-necked cerebral aneurysms with the Neuroform2 Treo stent. A prospective 6-month study", Neurosurg Focus 18(2):E4, February 2005, p. 1-5.) exerts remarkable mechanical flexibility in the longitudinal axis direction, the conformability is high and thus the open cell structures have been recognized as being effective for a stent structure that is placed in a tortuous tubular organ. However, for such an open cell structure, since a part of a strut of the stent may protrude radially outward in a flared shape when bent, there is a risk of damaging the tissue of a tubular organ in a body such as blood vessels when the stent is placed therein. On the other hand, regarding stents having a closed cell structure, Japanese Unexamined Application, Publication Nos. 2003-93518 and 2003-93519, and Randall T. Higashida, et al., "Initial Clinical Experience with a New Self-Expanding NitinolStent for the Treatment of Intracranial Cerebral Aneurysms: The Cordis Enterprise Stent", AJNR Am J Neuroradiol 26, August 2005, p. 1751-1756 disclose stents having closed cell structures that allow for a partial repositioning of a stent during operation, which had been difficult with open cell structures, and furthermore, Japanese Unexamined Patent Application, Publication No. 2010-264261 and Henkes H, et al., "A novel microcatheter-delivered, highly-flexible and fully-retrievable stent, specifically designed for intracranical use. Technical note.", Interventional Neuroradiology 9(4), 2003, p. 391-393, disclose stents having closed cell structures that allow for full repositioning of a stent during operation. For such a closed cell structure, although there is no risk of the strut of the stent protruding radially outward such as a stent having an open cell structure, the flexibility of the structure tends to be lacking. Therefore, there has been a risk of inhibiting the flow of liquid such as blood in tubular organs from flowing due to a stent buckling when applying the stent having a closed cell structure to a bent tubular organ. Furthermore, structurally speaking, since the stent having a closed cell structure is inferior to the stent having an open cell structure in terms of a reduction in diameter, the stent having a closed cell structure cannot handle placement of a stent into a tubular organ of small diameter of around 2 mm, a result of which there has been a risk of damaging a body tissue.

For this reason, as disclosed in PCT International Publication No. WO2010/090348 and Japanese Unexamined Patent Application (Translation of PCT Publication), Publication No. 2010-535075, a stent having a closed cell structure has been recently proposed which has a structure that compensates for the defect of the stent having a closed cell structure as mentioned above. However, for even such a stent, the minimum diameter in a state of being reduced radially is around 2 mm for the outer diameter thereof. Therefore, it cannot be recognized as sufficient for use in cerebral blood vessels. Furthermore, structurally speaking, a stent having a closed cell structure cannot be independently deformed locally. For this reason, changes in expansive force of a stent with respect to local changes of sectional diameters of the inner cavity at a site having a tapered structure tends to become great. Therefore, it has been desired to develop a stent with less change in expansive force with respect to the change in outer diameter.

In addition, in a case of the stent treatment for cerebral blood vessels, the expansion and recovery of a stent may be repeated in order to avoid misplacement. Furthermore, a stent left inside receives cyclic deformations (load) due to blood flow or the pulsating movement of a blood vessel wall. Therefore, excessive metallic fatigue may occur in the stent. Moreover, in a case in which a stent that is compressed at a high diameter reduction ratio such as the intracranial stent mentioned above is placed under such a severe load environment, the risk for metallic fatigue becomes very high compared to a stent employed for peripheral blood vessels to which the cyclic load due to pulsating movement, etc., is small or thick cardiac blood vessels. Since breakage of the stent due to such metallic fatigue leads to damage of blood vessel tissues and thus an accident during operation, it has been desired to develop a stent that is resistant to metallic fatigue.

As mentioned above, specifically for the stent treatment of cerebral blood vessels, it has been desired to provide a stent that can satisfy all of the various mechanical properties mentioned above. However, the conventional stents have not satisfied the various properties mentioned above.

In view of this, it is an object of the present invention to the solve problems that have existed in the conventional technologies, and provide a structure that can further improve various properties demanded in a stent.

In view of the abovementioned object, the present invention is a highly flexible stent including: a plurality of circular bodies having a wavy-line pattern and arranged side-by-side in an axis direction; and a plurality of coiled elements arranged between the circular bodies that are adjacent and extending in a spiral manner around an axis. All apices on opposite sides of the wavy-line pattern of the circular bodies that are adjacent are connected by way of the coiled elements. A knob portion is formed at each apex of the wavy-line pattern of the circular bodies, the knob portion including an extension portion extending in the axis direction having a width greater than a width of the coiled elements and a tip portion formed at a tip of the extension portion. The coiled element is connected with the knob portion. A slit is formed at a part of the extension portion of the knob portion, the slit extending in the axis direction from an inner peripheral portion at the apex of the wavy-line pattern of the circular body.

The abovementioned highly flexible stent is a so-called closed sell structure in which a plurality of circular bodies having a wavy-line pattern is arranged side-by-side in an axis direction and all apices at opposite sides of the wavy-line pattern of the circular bodies adjacent thereto are connected with the coiled element extending in a spiral manner around the axis. Therefore, even when a stent is placed at a curve portion of a tubular organ of a body, a strut constituting the stent does not protrude radially outward of the stent in a flared shape such as a stent having an open cell structure. Furthermore, the adjacent circular bodies are connected by way of a plurality of coiled elements extending in a spiral manner around the axis. Therefore, for these coiled elements, flexible bending deformation can occur in an axis direction like a coil spring. Furthermore, the circular body of a wavy-line pattern can be easily radially contracted in a circumferential direction, and the coiled element working like a coil spring is contracted in a radial direction by elongating in an axis direction. Therefore, the diameter reduction of the overall stent is facilitated. Additionally, for the abovementioned stent, the knob portion including an extension portion extending in the axis direction and having a width greater than a width of the coiled elements and a substantially semicircle portion formed at a tip of the extension portion is formed at each apex of the wavy-line pattern of the circular bodies. By making the range that contributes to a change of a length of an outer peripheral portion of an apex accompanied with expansion or diameter reduction longer, the strain (=an amount of deformation/length) occurring at an outer peripheral portion at the apex of the wavy-line pattern upon the expansion or diameter reduction of the stent is reduced.

Opposite side edges of the slit may be linear, extending substantially in parallel. The tip portion may be a substantially semicircle portion of substantially semicircular shape. The extension portion may extend linearly in the axis direction.

The coiled element may have a curve portion at both ends thereof and the coiled element may be connected with the circular body via the curve portion. The curve portion may be formed so that a tangential direction of the curve portion at a connecting end at which the coiled element connects with the circular body coincides with the axis direction.

A connecting end at which the apex located at one side in the axis direction of the wavy-line pattern of the circular body may connect with the coiled element and a connecting end at which the apex located at the other side in the axis direction of the wavy-line pattern of the circular body may connect with the coiled element are offset from the center of the apex to opposite sides in a circumferential direction.

The highly flexible stent may be formed from a super elastic alloy. The super elastic alloy may be a nickel titanium alloy. The highly flexible stent may be a stent to be placed in a cerebral blood vessel.

According to the present invention, since a so-called closed cell structure is adopted, it is possible to reduce the risk of damaging a tissue of a tubular organ by a strut constituting the stent protruding radially outward of the stent in a flared state like a stent having an open cell structure, even when the stent is placed at a curve portion in a tubular organ in a body. Furthermore, since the circular bodies of the wavy-line pattern are connected by way of the coiled element and flexible bending deformation can be made in the axis direction for the coiled element like a coil spring, the conformability of the overall stent with respect to a blood vessel structure is improved. Moreover, the circular body of the wavy-line pattern can be easily contracted in a circumferential direction, and the coiled element working like a coil spring is contracted in a radial direction by elongating in the axis direction. Therefore, the diameter reduction of the stent is facilitated. In addition, due to the knob portion, the strain occurring at an outer peripheral portion at the apex of the wavy-line pattern upon the expansion and diameter reduction of the stent is reduced. Therefore, it is possible to reduce the risk of metallic fatigue due to cyclic deformations at the apex occurring accompanied with blood flow in a blood vessel and the pulsating movement of a wall of a blood vessel, and thus it is possible to suppress the damage to the stent by improving the resistance to fatigue. According to the stent of the present invention with such a configuration, the conformability and the diameter reduction are high, and thus damage to the stent due to the metallic fatigue less occurs.

DETAILED DESCRIPTION OF THE INVENTION

Figure 1:
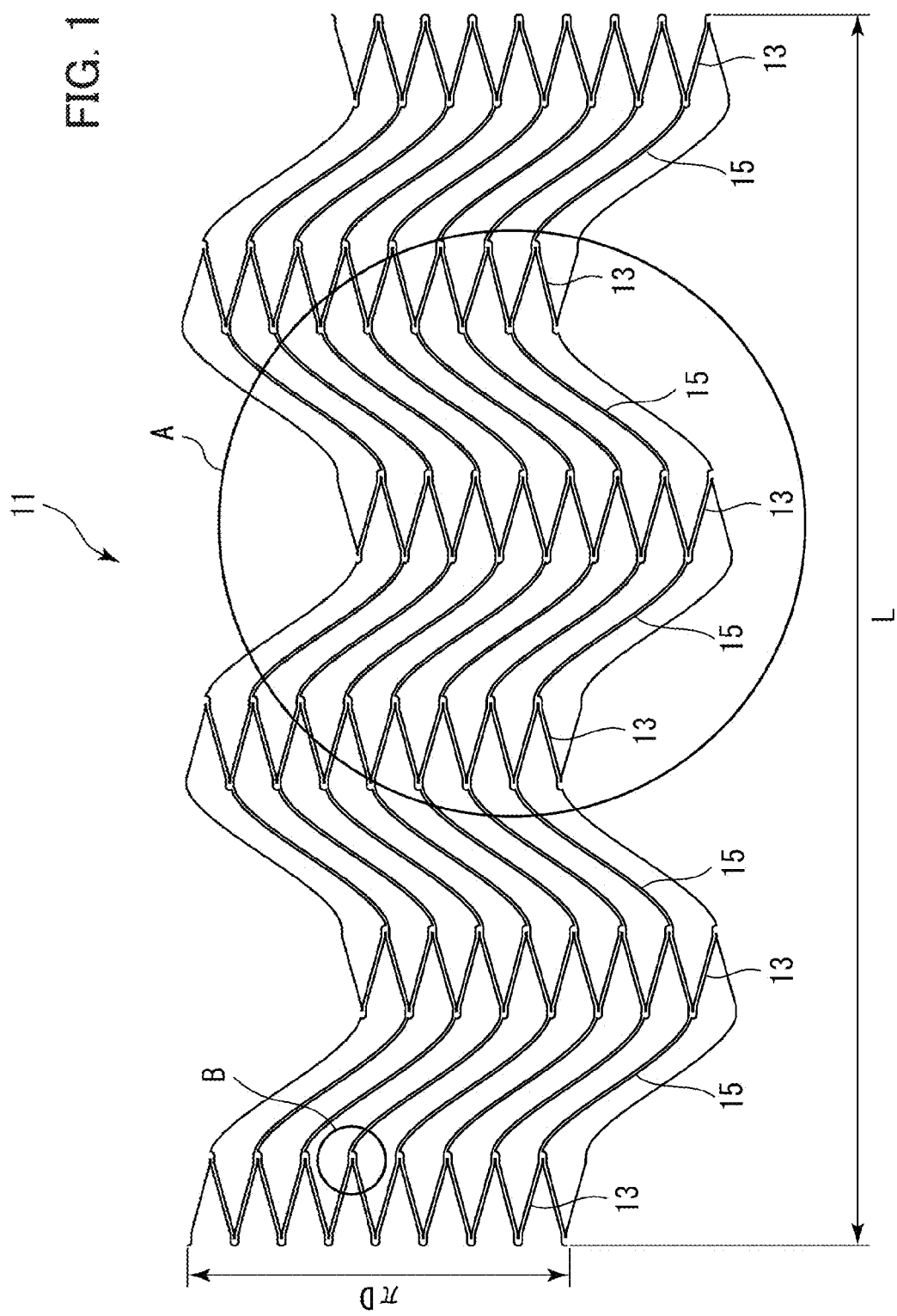
FIG. 1 is a view showing a highly flexible stent in an unloaded state according to an embodiment of the present invention expanded into a plane.
Figure 2:
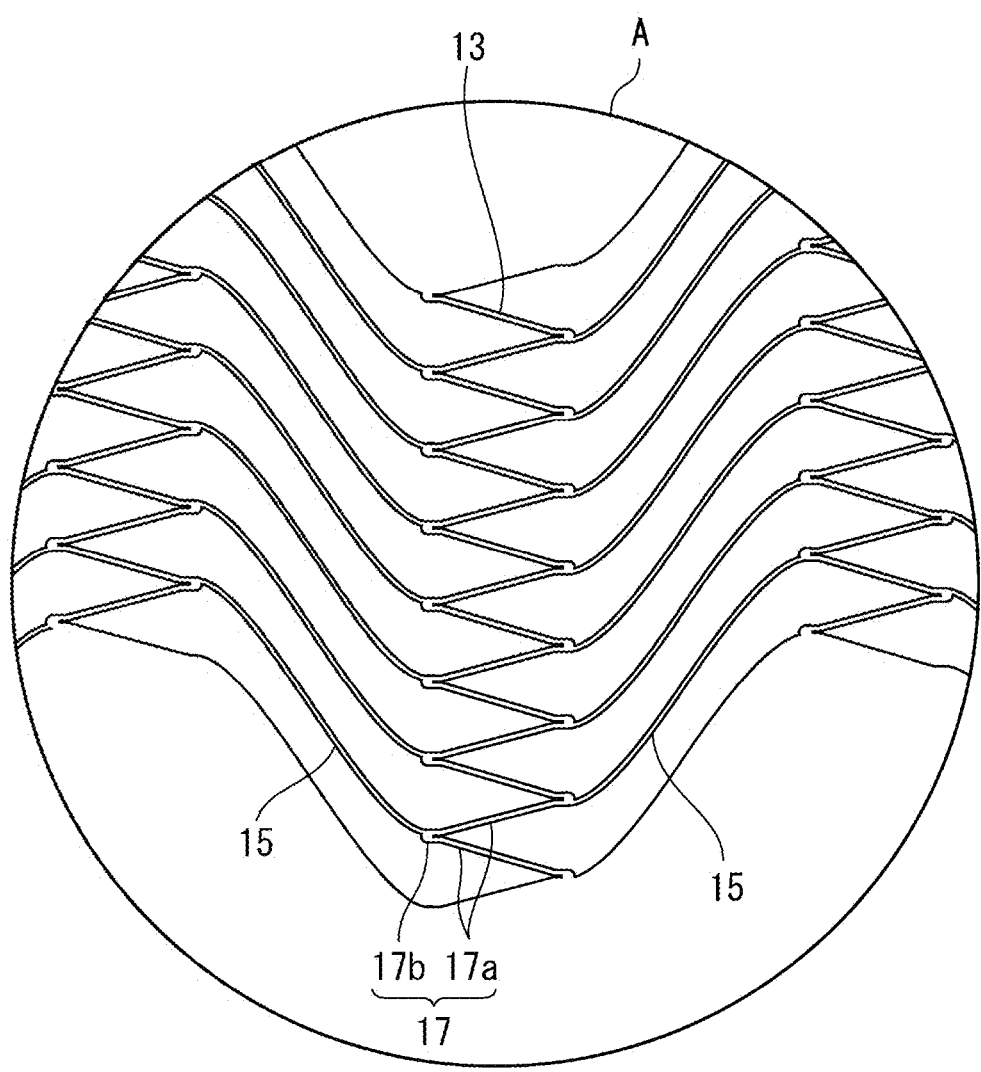
FIG. 2 is a view showing only a part A of the stent shown in FIG. 1.
Figure 3:
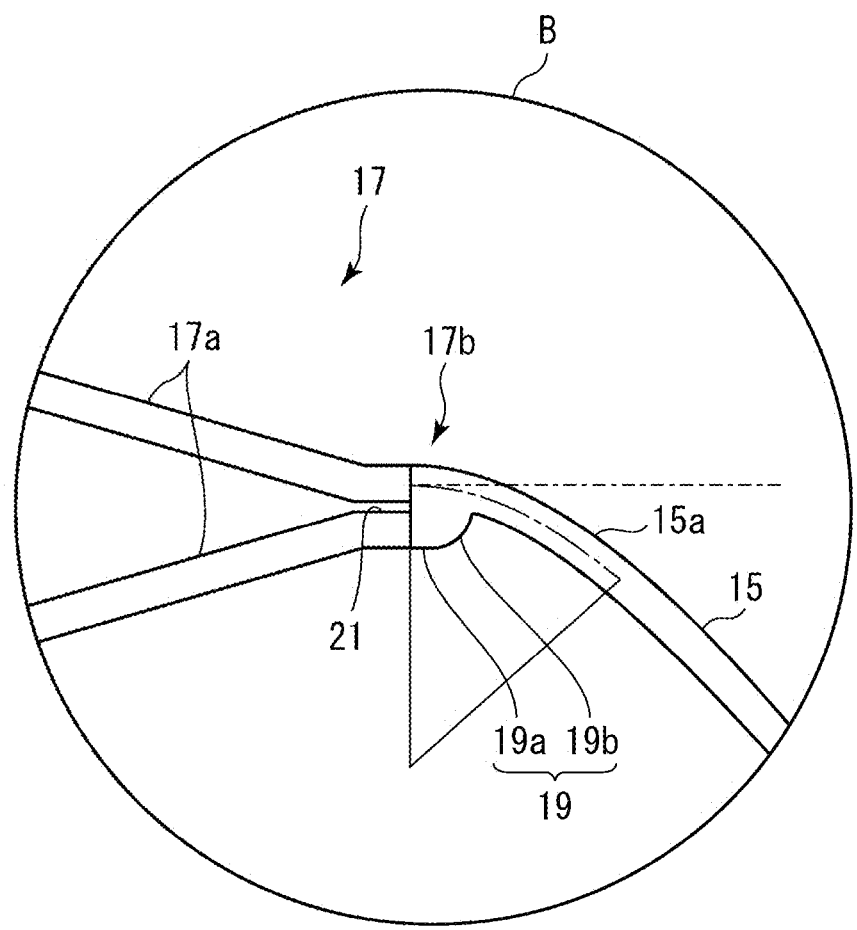
FIG. 3 is an enlarged view showing in detail a part B of the stent shown in FIG. 1.

In the following, embodiments of a highly flexible stent according to the present invention are described with reference to the drawings. With reference to FIGS. 1 to 3, an overall configuration of a highly flexible stent 11 according to one embodiment of the present invention is described.

The stent 11 is of a substantially cylindrical shape, with the diameter thereof being D and the length in a longitudinal axis direction being L. A peripheral wall of the stent 11 has a structure of a mesh pattern in which a plurality of closed cells having a congruent shape surrounded by wire-shaped materials is covering a circumferential direction. In FIG. 1, for the purpose of facilitating understanding of the structure of the stent 11, the stent 11 is illustrated in a state expanded in a plane. Here, in the present specification, the peripheral wall of the stent 11 refers to a part that separates the inside from the outside of a cylinder with a substantially cylindrical shape of the stent 11. Furthermore, the term "cell" also refers to an opening or a compartment that is a part enclosed by the wire-shaped material forming the mesh pattern of the stent 11.

The stent 11 is formed of material having biocompatibility such as stainless steel, tantalum, platinum, gold, cobalt, titanium, or alloys of these. It is particularly preferable for the stent 11 to be formed of materials having a super elastic property such as a nickel titanium alloy.

The stent 11 includes a plurality of circular bodies 13 that is arranged in a longitudinal axis direction (i.e. a center axis direction) and a plurality of coiled elements 15 that is arranged between the adjacent circular bodies 13 in the longitudinal axis direction. As shown in FIG. 2, the circular bodies 13 include a wavy-line pattern that is formed by connecting, in a circumferential direction, a plurality of waveform elements 17 of substantially V-shape made by coupling two leg portions 17a at an apex 17b. The plurality of coiled elements 15 are arranged at regular intervals around the center axis. Each of the plurality of coiled elements 15 extends in a spiral manner around the center axis. Both ends of each of the coiled elements 15 are connected with the apices 17*b*, respectively, at opposite sides of two adjacent circular bodies 13. It should be noted that all of the apices 17*b* at the opposite sides of the adjacent circular bodies 13 are connected to each other by the coiled element 15. Therefore, the stent 11 has a so-called closed cell structure. In other words, the two apices 17*b* that are arranged to be adjacent to each other along the wavy-line pattern among the three apices 17*b* connected to each other via the leg portions 17*a* along the wavy-line pattern at one of the circular bodies 13 that are adjacent thereto are respectively connected with the two apices that are arranged to be adjacent to each other along the wavy-line pattern among the three apices connected to each other via the leg portions 17*a* along the wavy-line pattern in the other one of the circular bodies 13 that are adjacent thereto by way of the coiled elements 15, to form cells. Then, all of the apices 17*b* of the wavy-line pattern of each of the coiled bodies 13 are shared with three cells.

The inventors found that the structure of the connecting portions of the circular bodies 13 and the coiled elements 15 greatly affects the characteristics of the stent 11. Therefore, the inventors achieve an improvement in the characteristics of the stent 11 by providing the characteristic structure described below at the connecting portions.

As illustrated in detail in FIG. 3, a knob portion 19 is formed at the apex 17*b* of the waveform element 17. The knob portion 19 includes an extension portion 19*a* extending linearly in the longitudinal axis direction and a substantially semicircle portion (tip portion) 19*b* formed at a tip thereof. The extension portion 19*a* has a width broader than the width of the coiled elements 15. Furthermore, at the apex 17*b* of the waveform element 17, a slit 21 is formed that extends in the longitudinal axis direction from an inner peripheral portion (a valley portion side of the left side of the waveform element 17 of substantially V-shape in FIG. 3). Therefore, two leg portions 17*a* are connected to the substantially semicircle portion 19*b* of the knob portion 19 and a region of the extension portion 19*a* in which a slit 21 is not provided, via linear portions extending substantially in parallel in the longitudinal axis direction. It should be noted that, although it is preferable for the tip portion 19*b* to be substantially a semicircle portion, it may not be a substantially semicircle portion (not illustrated).

A curve portion 15*a* is formed at both ends of each of the coiled elements 15. Both ends of each of the coiled elements 15 are respectively connected to the apices 17*b* (more specifically, the knob portion 19) at the opposite sides of two adjacent circular bodies 13 via the curve portion 15*a*. As shown in FIG. 3, the curve portions 15*a* of both ends of the coiled elements 15 have an arc-like shape. The tangential direction of the coiled elements 15 at a connecting end of the coiled element 15 and the apex 17*b* of the wavy-line pattern of the circular body 13 coincides with the longitudinal axis direction.

Furthermore, as illustrated in FIG. 3, the coiled element 15 is connected to a location that is offset in a circumferential direction from a center of the apex 17*b* of the circular body 13. Preferably, as shown in FIG. 2, the connecting end at which the apex 17*b* located at one side in the longitudinal axis direction of the wavy-line pattern of the circular body 13 connects with the coiled element 15 and the connecting end at which the apex 17*b* located at the other side in the longitudinal axis direction of the wavy-line pattern of the circular body 13 connects with the coiled element 15 are offset from the center of the apex 17*b* to opposite sides in the circumferential direction, respectively. For example, in the circular body 13 located at the center portion of FIG. 2, the connecting ends at which the apices 17*b* at the left side of the circular portion 13 connects with the coiled element 15 are offset upward from the center of the apices 17*b* in the drawing. On the other hand, the connecting end at which the apex 17*b* at the right side of the circular portion 13 connects with the coiled element 15 is offset downward from the center of the apices 17*b* in the drawing. Furthermore, the coiled elements 15 connected with the apices 17*b* located at one side among both ends in the longitudinal axis direction of the circular body 13 and the coiled elements 15 connected with the apices 17*b* located at the other side among both ends in the longitudinal axis direction of the circular body 13 have orientations opposite to each other about the center axis. For example, the coiled elements 15 located at one side among both ends in the longitudinal axis direction of the circular body 13 extend clockwise in a spiral manner, while the coiled elements 15 located at the other side among both ends in the longitudinal axis direction of the circular body 13 extends counter-clockwise in a spiral manner.

The stent 11 having such a configuration as described above realizes superior conformability and diameter reduction as well as damage of the stent not easily occurring due to metallic fatigue.

Structurally speaking, stents of the conventional closed cell structures disclosed in Japanese Unexamined Application, Publication Nos. 2003-93518, 2003-93519, and 2010-264261, Randall T. Higashida, et al., "Initial Clinical Experience with a New Self-Expanding NitinolStent for the Treatment of Intracranial Cerebral Aneurysms: The Cordis-Enterprise Stent", AJNR Am J Neuroradiol 26, August 2005, p. 1751-1756, and Henkes H, et al., "A novel microcatheter-delivered, highly-flexible and fully-retrievablestent, specifically designed for intracranical use. Technical note.", Interventional Neuroradiology 9(4), 2003, p. 391-393, lack flexibility, and thus there has been a risk of inhibiting blood flow due to a stent buckling in a tortuous blood vessel. Furthermore, if a stent is deformed locally, the deformation propagates not only in a radial direction of the stent, but also in an axial direction (the longitudinal axis direction), a result of which the stent cannot be deformed independently and locally. For this reason, the stent cannot be adapted to a complicated blood vessel structure such as an aneurysm and causes a space between a peripheral wall of the stent and a blood vessel wall, a result of which the stent easily slides in an intravascular lumen due to the deformation accompanied with the pulsation of a blood vessel, and may also cause movement (migration) of the stent after the placement therein.

On the other hand, in regard to the stent 11, since the circular body 13 having the wavy-line pattern can be easily deformed in a circumferential direction, the stent 11 can be flexibly adapted to contraction and expansion in a radial direction. Furthermore, the coiled element 15 connected between adjacent circular bodies 13 extends in a spiral manner around the center axis and deforms like a coiled spring. For this reason, when the stent 11 is bent, the coiled element 15 elongates at the outside of a bent portion and contracts at the inside of the bent portion. With such a configuration, flexible bending deformation of the overall stent 11 in the longitudinal axis direction is made possible. Furthermore, an external force given to the stent 11 locally and a resulting deformation propagate in a radial direction by way of the circular body 13 of the wavy-line pattern and propagate in a circumferential direction by way of the coiled element 15. Therefore, the circular body 13 and the coiled element 15 can be deformed almost independently at each site. With such a configuration, the stent 11 can be placed so as to be adapted to a site of pathology in a blood vessel structure even in a case in which the stent 11 is adapted to a site of pathology in a particular blood vessel such as a brain aneurysm. For example, in a case in which the stent 11 is placed at the site of a brain aneurysm, the circular body 13 of the wavy-line pattern is placed at a neck portion of a knob. In this way, the circular body 13 expands in a radial direction and develops in a space of the knob, so that the stent 11 can be fastened securely at this site. Furthermore, the coiled element 15 is in contact with a peripheral wall of a blood vessel along a shape of the blood vessel wall so as to serve as an anchor. Therefore, the risk of the stent 11 migrating is reduced. Furthermore, since the stent 11 has a closed cell structure, even when it is adapted to a bent site, it is possible to reduce the risk of the strut of the stent 11 protruding outward in a flared shape to damage a blood vessel wall and the strut of the stent 11 causing inhibition of blood flow.

In the following, operations and effects of each of the characteristic structures are described in detail. The slit 21 extending from the inner peripheral portion of the apex 17b of the waveform element 17 of the circular body 13 of the stent 11 exerts an effect of improving diameter reduction of the stent 11.

Figure 4A:
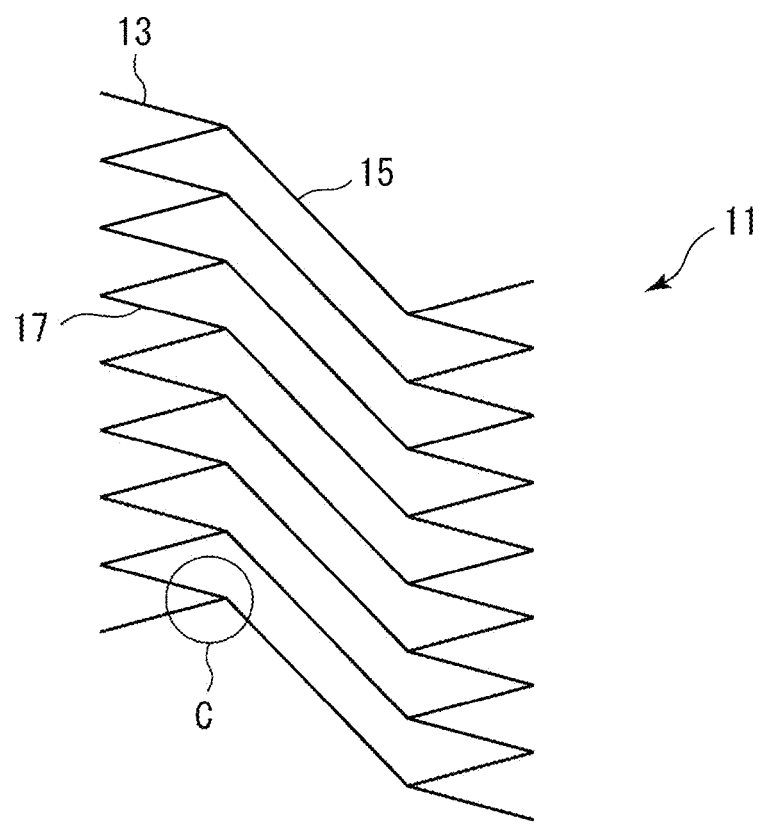
FIG. 4A is a schematic view schematically showing an expanded state of a highly flexible stent according to the present invention.
Figure 4B:
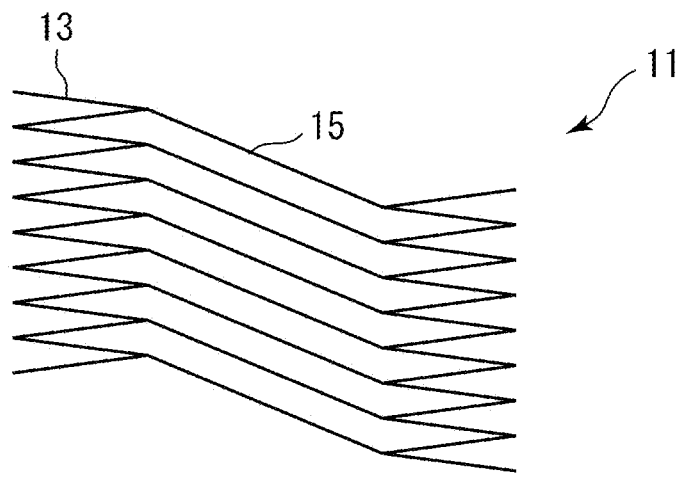
FIG. 4B is a schematic view schematically showing a radially reduced (crimped) state of a highly flexible stent according to the present invention.
Figure 5:
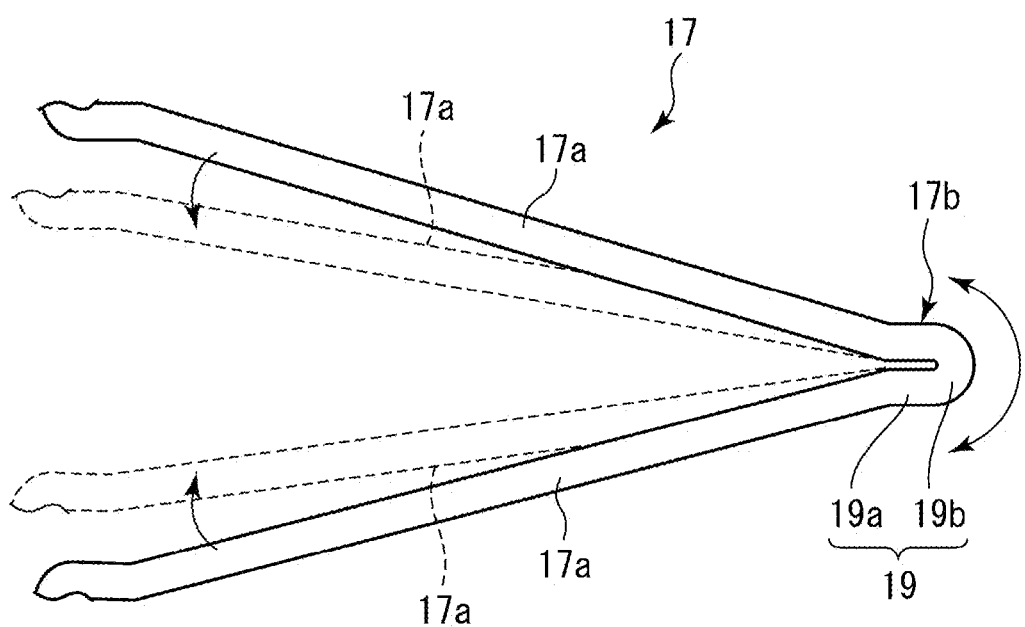
FIG. 5 provides illustrative views showing the matter of deformation occurring at an apex of a waveform element of the circular body of a stent when the stent shown in FIG. 1 is radially reduced.
Figure 6A:
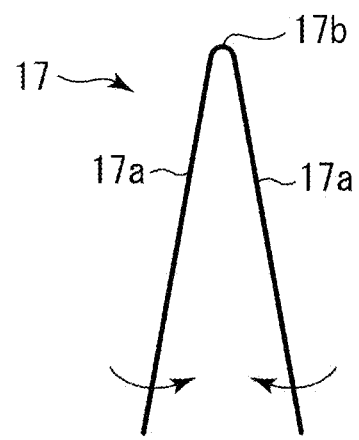
FIG. 6A is a schematic view showing a deformation state of a waveform element during diameter reduction in a case in which a slit is not provided at an apex of a waveform element of the circular body of a stent.
Figure 6B:
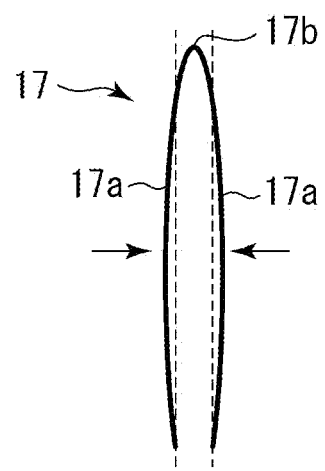
FIG. 6B is a schematic view showing a deformation state of a waveform element during diameter reduction in a case in which a slit is not provided at an apex of a waveform element of the circular body of a stent.
Figure 7A:
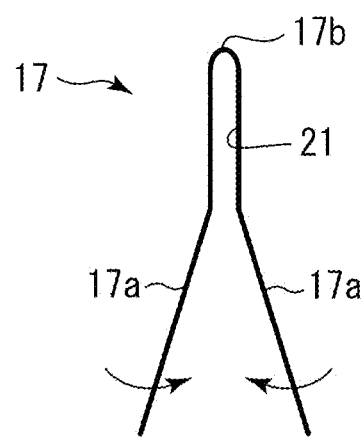
FIG. 7A is a schematic view showing a deformation state of a waveform element during diameter reduction in a case in which a slit is provided at an apex of a waveform element of the circular body of a stent.
Figure 7B:
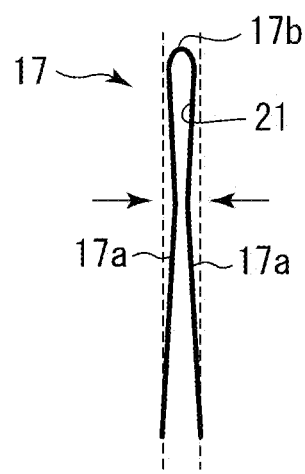
FIG. 7B is a schematic view showing a deformation state of a waveform element during diameter reduction in a case in which a slit is provided at an apex of a waveform element of the circular body of a stent.

As illustrated in FIGS. 4A and 4B, when the stent 11 is deformed from an expanded state to a radially reduced state (a crimped state), the wavy-line pattern of the circular body 13 is folded so as to enter a compressed state, and the coiled element 15 is made to be laid in the longitudinal axis direction as a coiled spring and enters a state being pulled in the longitudinal axis direction. When viewing a single piece of the waveform element 17 of the wavy-line pattern of the circular body 13 of the stent 11, as illustrated in FIG. 5, the waveform element 17 deforms to be open and closed such as a tweezer upon the diameter reduction and expansion of the stent 11. In a case in which the slit 21 is not provided at a valley side portion of a base of the waveform element 17 (an inner peripheral portion of the apex 17b) as shown in FIG. 6A, when deforming the stent 11 so as to close the waveform element 17 to radially reduce the stent 11, center portions of the leg portions 17a swell outward in a barrel-like shape and thus easily deform, as illustrated in FIG. 6B. If the waveform element 17 is swollen in a barrel-like shape in this way, the swollen portions in a barrel-like shape of the leg portions 17a of the adjacent waveform elements 17 in a circumferential direction in the circular body 13 come into contact with each other when radially reducing the stent 11. This contact prevents the stent 11, more specifically, the circular body 13, from radially reducing, which leads to the degradation of the ratio of diameter reduction. On the other hand, the slit 21 is provided at a base portion of the waveform element 17 of the circular body 13 as illustrated in FIG. 7A in the stent 11. Therefore, when radially reducing the stent 11, as illustrated in FIG. 7B, the stent 11 is deformed so that the leg portions 17a of the waveform element 17 adjacent in a circumferential direction in the circular body 13 bring less contact with each other, a result of which the ratio of diameter reduction can be improved.

The knob portion 19 provided at the apex 17b of the waveform element 17 of the circular body 13 of the stent 11 exerts an effect of reducing metallic fatigue.

As described above, the waveform element 17 deforms to be open and closed such as a tweezer upon the diameter reduction and expansion of the stent 11 as shown in FIG. 5. Therefore, upon crimping and expansion of the stent 11, the deformation concentrates on the apex so that the strain due to material deformation occurs intensively at this part. Therefore, in a case of repeating diameter reduction and expansion of the stent 11 or in a case in which the stent 11 repeatedly receives load accompanied with deformation due to blood flow in a blood vessel or pulsation of a wall of a blood vessel, excessive metallic fatigue tends to occur at the apex 17b of the waveform element 17. Therefore, in order to reduce the risk of metallic fatigue occurring, the shape of the apex 17b is modified for an improvement in the stent 11 so as to reduce the strain occurring at the apex 17b.

Upon diameter reduction and expansion of the stent 11, since the waveform element 17 becomes opened and closed around a valley side portion of the base portion (inner peripheral portion), the strain of the apex 17b of the waveform element 17 occurs greatly particularly at an outer peripheral portion in the region of the apex 17b (an outside of the apex 17b shown by a curve with arrows at the both ends of the curve in FIG. 5). Here, the strain e is represented by the following equation with the length before deformation being $l_0$ and the deformation amount being u.

$$e = u/l_0$$

Figure 8:
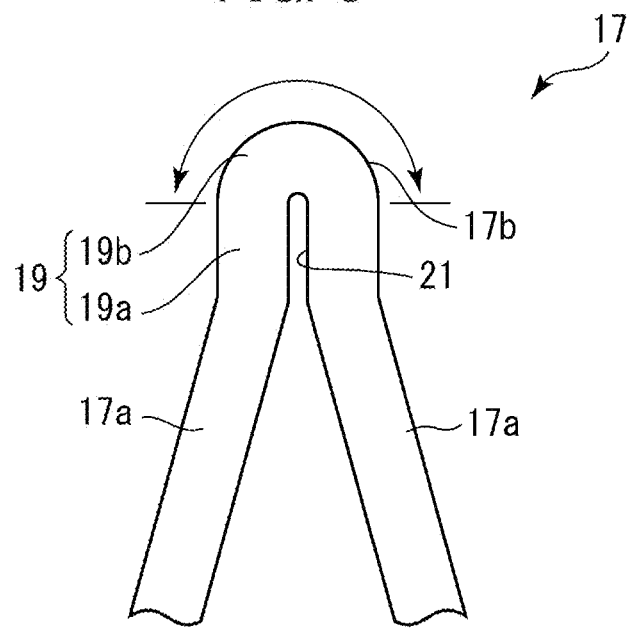
FIG. 8 is a partially enlarged view showing a first embodiment of an apex of a waveform element of the circular body of the stent shown in FIG. 1.
Figure 9:
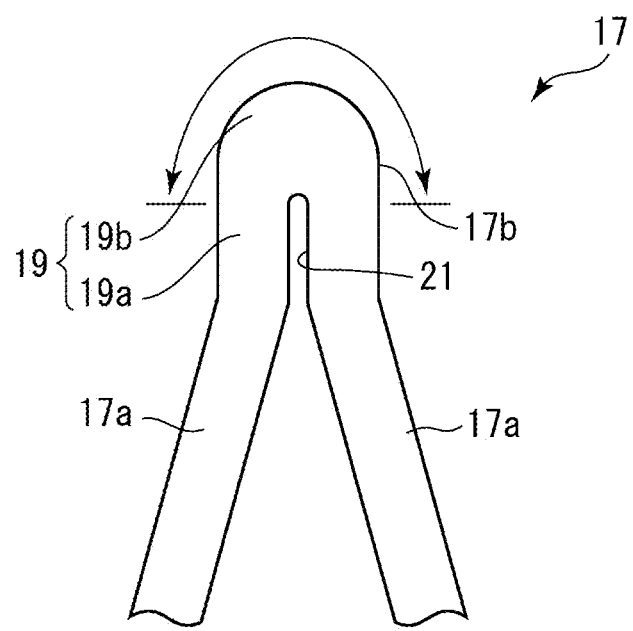
FIG. 9 is a partially enlarged view showing a second embodiment of an apex of a waveform element of the circular body of the stent shown in FIG. 1.
Figure 10:
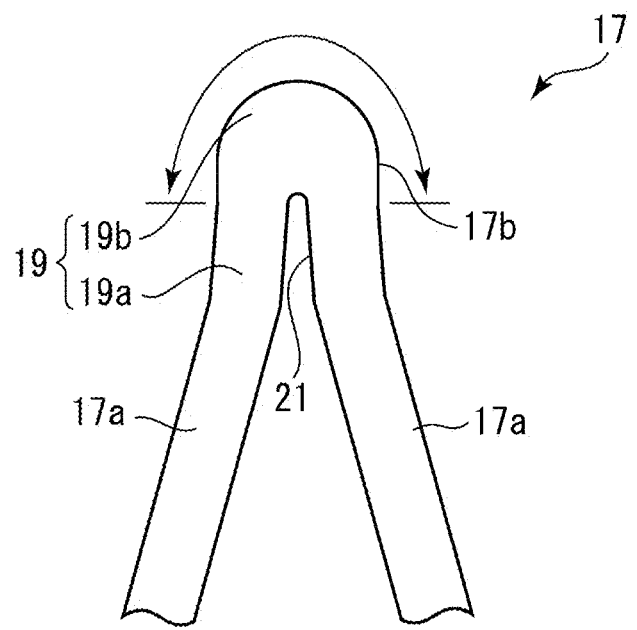
FIG. 10 is a partially enlarged view showing a third embodiment of an apex of a waveform element of the circular body of the stent shown in FIG. 1.

Therefore, in order to reduce the risk of metallic fatigue occurring at the apex 17b of the stent 11, it is only necessary to reduce the strain occurring at the apex 17b upon diameter reduction and expansion of the stent 11. When assuming that the same deformation amount u is imparted upon diameter reduction, it is possible to reduce the strain occurring at the apex 17b by increasing the length corresponding to $l_0$. Furthermore, the deformation of the waveform element 17 is made at a valley side portion of the base portion of the waveform element 17 (inner peripheral portion), and a portion that substantially contributes to the deformation is a peak side portion of the apex 17b of the waveform element 17 (the range shown by a curve with arrows at both ends of the curve on the upper side in FIGS. 8 to 10), specifically an outer peripheral portion. Therefore, as shown in FIGS. 8 to 10, it is configured in the stent 11 such that the knob portion 19 including the extension portion 19a and the substantially semicircle portion 19b and having a width greater than the width of the coiled element 15 is formed at the apex 17b to allow the apex portion 17b to extend in the longitudinal axis direction. More specifically, the extension portion 19a extending in the longitudinal axis direction is provided between the leg portions 17a of the waveform element 17 and the substantially semicircle portion 19b forming the apex 17b so as to offset the apex 17b outward from the valley side portion of the base portion of the waveform element 17 (inner peripheral portion) as a deformation base point. The outer peripheral portion of the apex 17b is made to extend with such a configuration. In order to prevent adjacent knob portions 19 in a circumferential direction from blocking diameter reduction due to coming into contact with each other upon diameter reduction, as shown in FIGS. 8 to 10, it is desirable for the extension portion 19a to be formed by way of a linear portion extending in the longitudinal axis direction.

It should be noted that, in a case in which the slit 21 extending from the inner peripheral portion of the apex 17b is formed at the apex 17b of the waveform element 17, as shown in FIG. 7, the deformation of the waveform element 17 takes place around a tip of the slit 21 (an upper end of the slit 21 in FIGS. 8 to 10). A main portion involved in the deformation accompanied with crimping and expansion corresponds to a portion that is located more outside than the tip of the slit 21 of the waveform element 17. Therefore, it is more preferable to configure such that the length of the extension portion 19a is longer than the length of the slit 21 and the extension portion 19a extends beyond the tip of the slit 21, as shown in FIG. 9, than to configure such that the length of the extension portion 19a is the same as the length of the slit 21 or shorter than the length of the slit 21, as shown in FIG. 8. As shown in FIGS. 8 and 9, opposite side edges of the slit 21 are linear extending substantially in parallel. It should be noted that, as shown in FIG. 10, the opposite side edges of the slit 21 may not extend substantially in parallel (for example, the opposite side edges may become slightly wider toward the leg portions 17a). In addition, the opposite side edges of the slit 21 may not be linear (not illustrated).

Furthermore, in a case of the stent 11 being formed of a super elastic alloy such as a nickel titanium alloy, as shown in FIG. 9, it can be configured so as to provide the knob portion 19 at the apex 17b of the waveform element 17 of the circular body 13 of the stent 11 and have the length of the extension portion 19a of the knob portion 19 longer than the length of the slit 21. With such a configuration, it is possible to extract the super elastic property of the super elastic alloy to a maximum extent and suppress a change in expansive force with respect to a change in the outer diameter of the stent 11.

Figure 11:
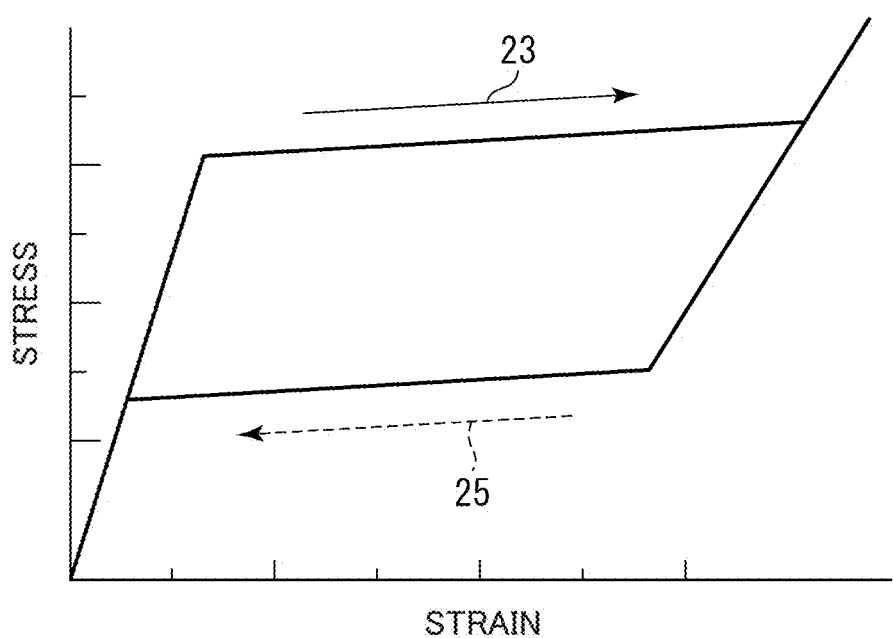
FIG. 11 is a graph showing a stress-strain curve of a super elastic alloy.
Figure 12:
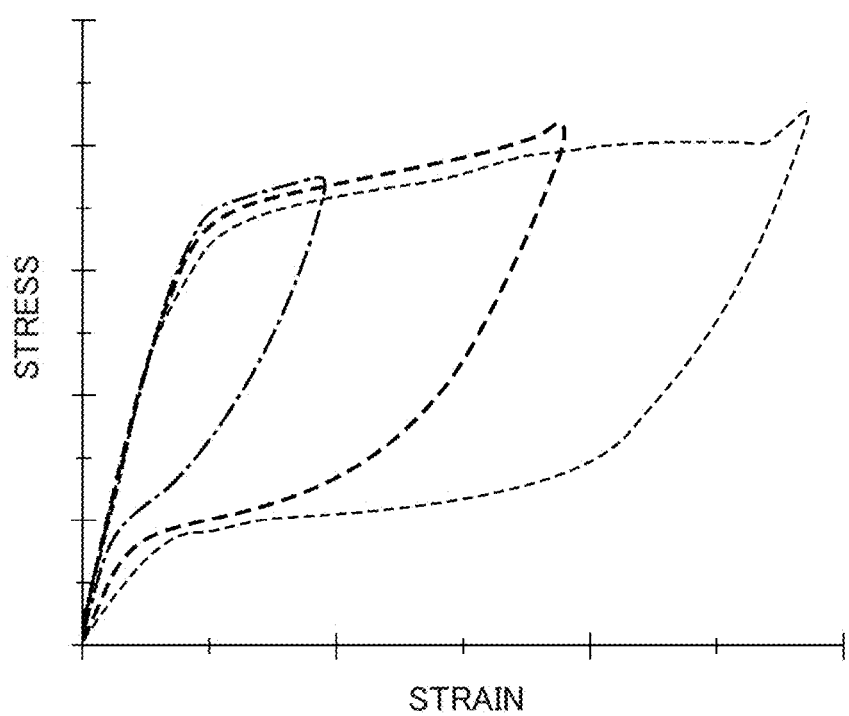
FIG. 12 is a graph showing a stress-strain curve for each of the cases varying the degree of strain applied to a super elastic alloy.

In a case of adopting the super elastic alloy as a material, when stress loading is applied to the material and exceeds the yield stress of the material, it exhibits a behavior of a loading process along the arrow 23 in the stress-strain curve shown in FIG. 11. At this time, the super elastic alloy causes phase transformation from austenite phase to martensite phase. Moreover, when unloading from this state, it exhibits a behavior of an unloading process along the arrow 25 in the stress-strain curve shown in FIG. 11, the phase transformation is then caused from austenite phase to martensite phase, and thus the strain imparted in the loading process is recovered in the unloading process. Furthermore, as shown in FIG. 12, the phase transformation to martensite phase is induced easier with higher stress loading applied to a material, and a deformation region of a gentle unloading curve along the arrow 25 of FIG. 11 becomes longer. This behavior of the unloading process corresponds to a change in the expansive force (radial force) acquired when unloading after the stent 11 being radially reduced. Therefore, if it is possible to make the region in which the curve changes gently in the unloading process shown in FIG. 11 longer, the stent 11 can be acquired with less change in the expansive force even with different diameters of blood vessels.

Figure 13:
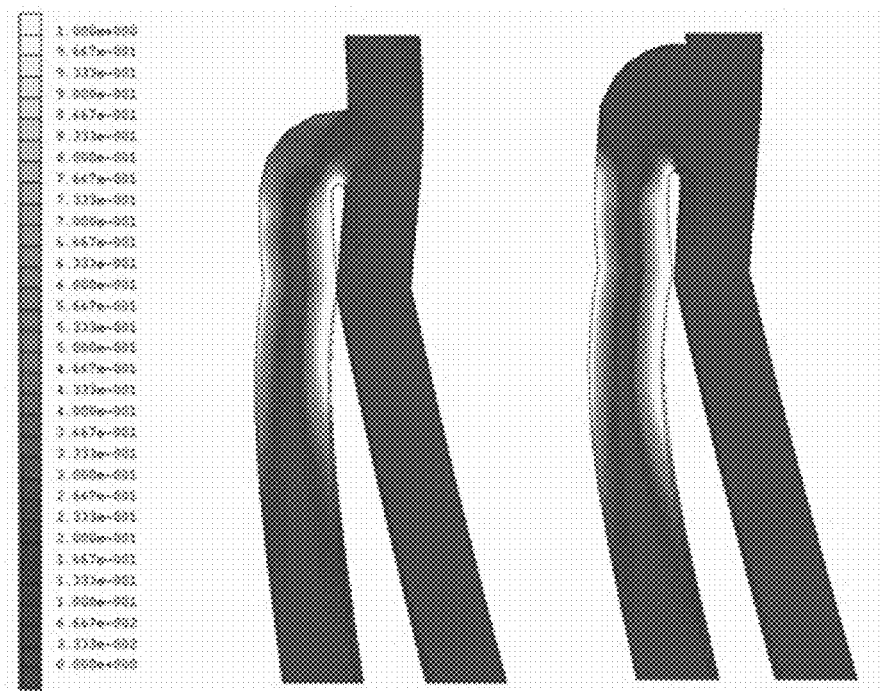
FIG. 13 is a distribution diagram for the volume fraction of a region in which phase transformation to a martensite phase occurs in a waveform element having an apex of a first embodiment shown in FIG. 8 and a waveform element having an apex of a second embodiment shown in FIG. 9.

The inventors found that, in a case in which the slit 21 is provided at the apex 17b of the waveform element 17 of the circular body 13 of the stent 11, it is configured such that the length of the extension portion 19a of the knob portion 19 provided at the apex 17b is longer than the length of the slit 21 so that the volume ratio of the phase transformation to martensite phase at a neighboring portion of the slit 21 upon loading increases. FIG. 13 is a view illustrating a volume fraction calculated by way of simulation of a region, of the apex 17b of the waveform element 17 of the stent 11 upon diameter reduction, in which the phase transformation to martensite phase is caused. The left side of FIG. 13 shows the result of a case in which the length of the extension portion 19a is substantially the same as the length of the slit 21 (the distance from the tip of the slit 21 to the apex of the substantially semicircle portion of the knob portion 19 is 0.06 mm) as shown in FIG. 8. The right side of FIG. 13 shows the result of a case in which the length of the extension portion 19a is longer than the length of the slit 21 (the distance from the tip of the slit 21 to the apex of the substantially semicircle portion of the knob portion 19 is 0.11 mm) as shown in FIG. 9. It is found that the stent 11 shown on the right side of FIG. 13 has a larger white region (specifically, at an outer region of the extension portion 19a around the slit 21), which indicates that the volume fraction of a region in which the phase transformation is caused to martensite phase is high. Therefore, it is configured for the stent 11 to include the waveform element 17 having the apex 17b as shown in FIG. 9, so that it is possible to realize the stent 11 for which a change in expansive force with respect to a change in a diameter of the stent 11 is gentle and with less change in expansive force with different diameters of blood vessels.

The curve portion 15a provided at both ends of the coiled element 15 of the stent 11 makes the deformation of the coiled element 15 at the connected portion with the circular body 13 further smoother, a result of which it exerts an effect of further improving the diameter reduction of the stent 11.

Figure 14:
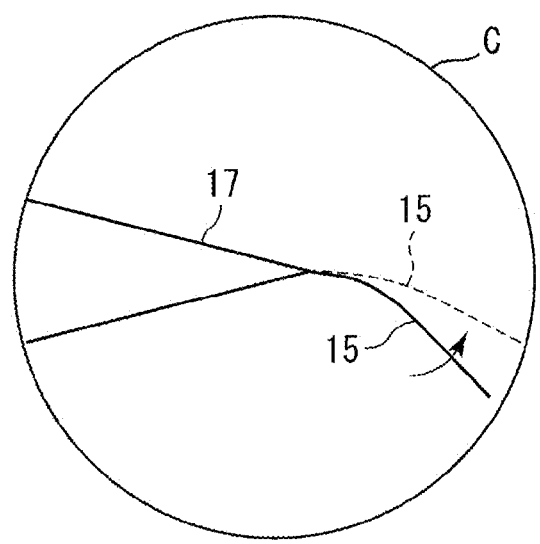
FIG. 14 is an enlarged view of a part C of the stent shown in FIG. 4 and schematically shows the behavior of a connecting end when a coiled element is deformed during diameter reduction.

When radially reducing the stent 11, as shown in FIG. 4A, the coiled element 15 is deformed so as to elongate in the longitudinal axis direction. Therefore, in order to improve the flexibility of the stent 11, it is necessary to design the stent 11 so that the connecting portion of the apex 17b of the circular body 13 and the coiled element 15 becomes flexible. In stent 11, the curve portion 15a having a circular shape at both ends of the coiled element 15 is provided and the apex 17b of the circular body 13 is connected with the coiled element 15 via the curve portion 15a. Upon the diameter reduction of the stent 11, as shown in FIG. 14, the curve portion 15a is bent and deformed, a result of which the flexible deformation of the coiled element 15 becomes possible, which leads to an improvement in diameter reduction.

Figure 15:
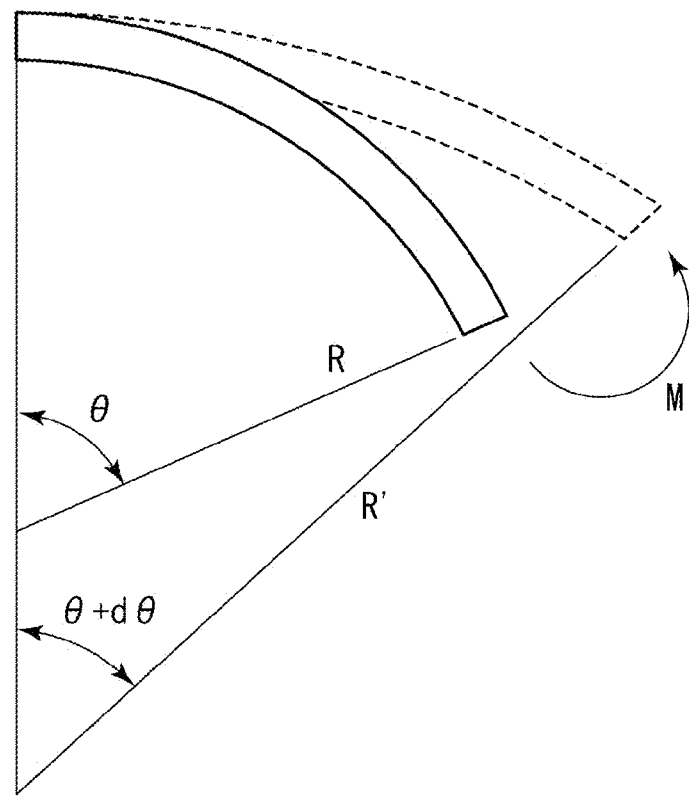
FIG. 15 is a schematic view showing a state before deformation (solid line) and a state after deformation (dashed line) of a curved beam when a bending moment is received.

As shown in FIG. 15, the deformation of the curve portion 15a can approximate the deformation of a thin-walled curved beam. An angular strain (angle change ratio) ω of the deformation when a thin-walled curved beam having a radius of curvature R receives a bending moment M to become a radius of curvature R' is represented as follows with the condition of a curved beam being an arc, and defining the center angle θ before bending changes as θ+dθ.

$$\omega = \Delta d\theta/d\theta = MR/EIx$$

Here, E is Young's modulus and Ix is a constant. Therefore, when the curvature radius R is greater, greater angle strain is acquired with respect to the bending moment of the same degree, and thus the coiled element 15 can be deformed flexibly.

Furthermore, the configuration in which the tangential direction of the curve portion 15a at the connecting end at which the coiled element 15 connects with the apex 17b of the circular body 13 coincides with the longitudinal axis direction exerts an effect of making a change in expansive force with respect to a change in the diameter of the stent 11 gentle.

The coiled element 15 is deformed like a coiled spring to elongate in the longitudinal axis direction, which allows for the deformation in a radial direction accompanied with the diameter reduction of the stent 11. Therefore, by matching the tangential direction of the curve portion 15a at the connecting end at which the circular body 13 connects with the coiled element 15 with the longitudinal axis direction, it becomes possible to effectively exhibit deformation properties of the coiled element 15 in the longitudinal axis direction. Since it is configured such that the coiled element 15 can be deformed smoothly in the longitudinal axis direction, the diameter reduction and expansion of the stent 11 is facilitated. Furthermore, since natural deformation in the longitudinal axis direction of the coiled element 15 is facilitated, it is possible to prevent unpredictable deformation resistance from occurring, which exerts an effect of making the response of expansive force with respect to a change in the diameter of the stent 11 gentle.

The configuration in which the connecting end at which the circular body 13 connects with the coiled element 15 is offset from the center of the apex 17b of the circular body 13 in a circumferential direction exerts an effect of improving the delivery and expansion performance of the stent 11. The configuration in which the connecting end at which the apex 17b located at one side in the longitudinal axis direction of the circular body 13 connects with the coiled element 15 and the connecting end at which the apex 17b located at the other side in the longitudinal axis direction of the circular body 13 connects with the coiled element 15 are offset to the opposite sides in the circumferential direction, further improves the delivery and expansion performance of the stent 11.

The stent 11 is inserted into a catheter in a state of being radially reduced, extruded by an extruder such as a pusher and moved in the catheter, and expanded at a site of pathology. At this moment, the force in the longitudinal axis direction applied by the extruder interacts between the circular body 13 and the coiled element 15 of the stent 11 to propagate over the entire stent 11. Since the connecting end at which the apex 17b of the circular body 13 connects with the coiled element 15 is offset from the center of the apex 17b in a circumferential direction, when a force in the longitudinal axis direction is transmitted from the coiled element 15 to the circular body 13, the force is smoothly transmitted to one leg portion 17a that constitutes the waveform element 17 of the circular body 13. Therefore, the transmissibility of the force in the longitudinal axis direction is improved. Furthermore, in a case in which the connecting end at which the apex 17b located at one side in the longitudinal axis direction of the circular body 13 connects with the coiled element 15 and the connecting end at which the apex 17b located at the other side in the longitudinal axis direction of the circular body 13 connects with the coiled element 15 are offset to opposite sides in the circumferential direction, as shown in FIG. 2, for example, in a case in which the connecting ends at which the apices 17b located at the left side of the circular portion 13 located at the center of FIG. 2 connects with the coiled element 15 are offset upward from the center of the apices 17b and the connecting end at which the apices 17b located at the right side of the circular portion 13 connects with the coiled element 15 are offset downward from the center of the apices 17b, the distance for which the force in the longitudinal axis direction transmitted from the connecting end at which the coiled element 15 on the left side connects with the apices 17b of the circular body 13 reaches the connecting end at which the coiled element 15 at the right side connects with the apices 17b of the circular body 13 via the leg portions 17a of the circular body 13 can be shortened. Then, the force in the longitudinal axis direction to the stent 11 is transmitted more smoothly. Therefore, during the migration of the stent in a lumen of a catheter and the extrusion of the stent from the catheter, buckling of the stent 11 due to the force from the extruder in the longitudinal axis direction occurs less, which facilitates the delivery and expansion of the stent 11.

The stent 11 having the abovementioned structure is produced by laser-machining a material having biocompatibility, and more preferably, a tube made of a super elastic alloy. When producing a stent made of a super elastic alloy tube, in order to reduce production cost, it is preferable to produce the stent 11 by expanding an approximately 2 to 3 mm tube to a desirable diameter and performing shape-memory treatment after laser-machining. However, the method of producing the stent 11 is not limited to laser-machining and includes other methods such as cutting processing.

Next, a method of using the stent 11 is described. A catheter is inserted into a blood vessel of a patient and the catheter is delivered to a site of pathology. Then, the stent 11 is radially reduced (crimped) and placed in the catheter. The property of the diameter reduction of the stent 11 is improved by multiple and synergistic effects due to the wavy-line pattern of the circular body 13, the slit 21 formed at the apex 17b of the circular body 13, the curve portion 15a of the coiled element 15, and the configuration in which a tangential direction of the curve portion 15a at a connecting end coincides with the longitudinal axis direction. Therefore, it becomes easier to insert the stent 11 into a narrow catheter and also becomes possible to apply the stent 11 to narrower blood vessels, as compared to conventional stents.

Next, the stent in a state of being radially reduced is pushed out along a lumen of the catheter using an extruder such as a pusher and the stent 11 is extruded from a tip of the catheter and expanded at a site of pathology. The flexibility upon delivery of the stent 11 is improved by multiple and synergistic effects due to the configuration in which a plurality of the circular bodies 13 are connected with the coiled elements 15, the curve portion 15a of the coiled element 15, and the configuration in which a tangential direction of the curve portion 15a at a connecting end coincides with the longitudinal axis direction. Therefore, even in a case in which the catheter is inserted into a tortuous blood vessel, the stent 11 is deformed flexibly along the catheter and the stent 11 can be easily delivered to a site of pathology. Furthermore, since it is configured so that the stent 11 has a closed cell structure and the strut thereof does not protrude outward in a flared shape, unnecessary contact between a lumen of the catheter and the stent 11 can be avoided. Furthermore, with the configuration in which the connecting end at which the apex 17b of the circular body 13 connects with the coiled element 15 is offset from the center of the apex 17b (more specifically, the configuration in which the connecting end at one side of the longitudinal axis direction of the circular body 13 and the connecting end at the other side in the longitudinal axis direction are offset to opposite sides in the circumferential direction, respectively), the force by the extruder in the longitudinal axis direction can be transmitted effectively to the stent 11 and it is also possible to suppress buckling of the stent occurring due to the force in the longitudinal axis direction. Therefore, the stent 11 possesses superior deliverability.

Moreover, by configuring so that the stent 11 has the knob portion 19 provided at the apex 17b of the circular body 13, it is possible to suppress the occurrence of metallic fatigue, and thus it is possible to suppress the damage to the stent 11 due to the repetition of diameter reduction and expansion of the stent 11 caused by misplacement and cyclic deformations of the stent 11 caused by a blood flow or a pulsating movement of a blood vessel, etc.

Figure 16:
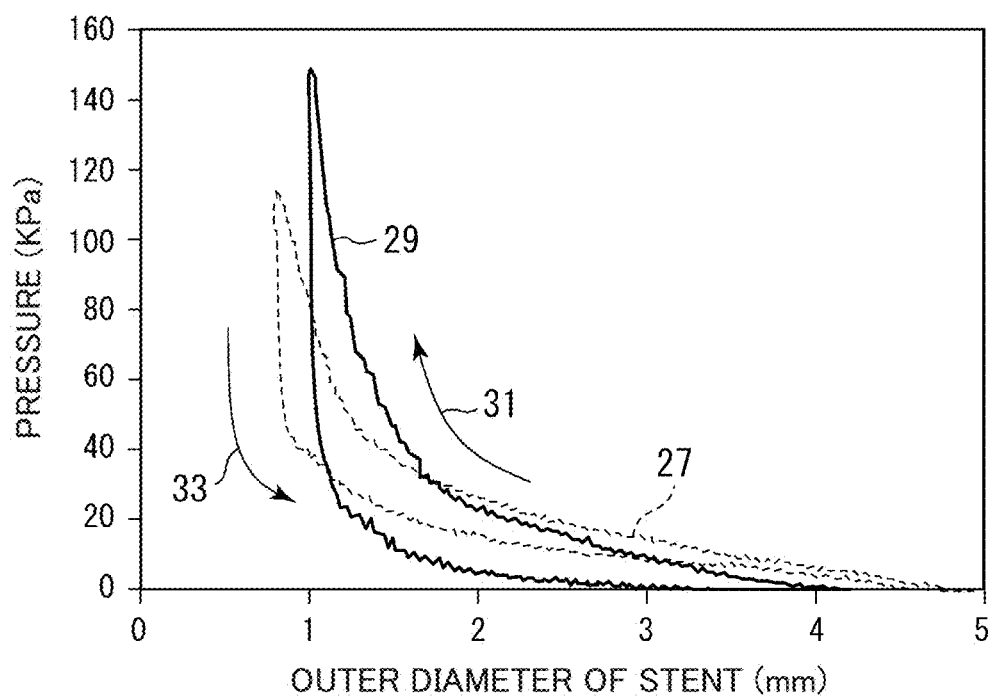
FIG. 16 is a graph showing a relationship between the amount of change in diameter of a stent and the force in the radial direction applied to a blood vessel by the stent, by comparing a stent according to an embodiment shown in FIG. 1 and a stent of prior art.

In addition, the flexibility of the stent 11 is improved by multiple and synergistic effects due to the configuration in which the region in which the phase transformation is caused to martensite phase at a deformation portion upon crimping increasing by providing the slit 21 at the apex 17b of the circular body 13, the curve portion 15a of the coiled element 15, and the configuration in which a tangential direction of the curve portion 15a at a connecting end coincides with the longitudinal axis direction, and as shown in FIG. 16, the change in expansive force with respect to the change in the diameter of the stent 11 becomes gentle in the unloading process. As a result of this, the conformability of the stent 11 can be improved and it is also possible to place the stent 11 at a site where the diameter of a blood vessel changes locally such as a tapered blood vessel, without placing an unnecessary load on the blood vessel.

It should be noted that FIG. 16 is a graph showing the relationship between a diameter of a stent and pressure applied to a blood vessel. In FIG. 16, the curved line shown by the dashed line 27 shows the characteristics in a case in which a stent having a conventional open cell structure with an outer diameter of 4.5 mm is radially reduced to no more than 1 mm and then unloaded, and the curved line shown by the solid line 29 shows the characteristics in a case in which the stent 11 with an outer diameter of 4.2 mm according to the present invention is radially reduced to no more than an outer diameter of 1 mm and then unloaded. The arrow 31 indicates a loading process and the arrow 33 indicates an unloading process. More specifically, in the unloading process, it is found that a change in pressure with respect to the outer diameter of the stent 11 is gentle and lowered, as compared to a conventional stent.

Although the stent 11 according to the present invention is described above with reference to the embodiments illustrated in the drawings, the present invention is not limited to the embodiments illustrated in the drawings. For example, in the embodiments illustrated in the drawings, although the stent 11 is configured by connecting six circular bodies 13 by way of the coiled elements 15, the stent 11 may be configured by connecting five or fewer circular bodies 13 or seven or more circular bodies 13 by way of the coiled elements 15. Furthermore, in the embodiments illustrated in the drawings, although the characteristic structure such as the knob portion 19, the slit 21, the curve portion 15a, and the like are adapted to a stent including the circular bodies 13 having the wavy-line pattern, the present invention is not limited thereto. It is also possible to apply the characteristic structure such as the knob portion 19, the slit 21, the curve portion 15a, and the like, to a stent with a structure including a spiral body with a wavy-line pattern and having apices of the wavy-line pattern of the spiral body to be connected by way of the coiled element.

What is claimed is:
1. A highly flexible stent comprising:
a plurality of circular bodies having a wavy-line pattern and arranged side-by-side in an axis direction; and
a plurality of coiled elements arranged between the circular bodies that are adjacent and extending in a spiral manner around an axis,
wherein all apices on opposite sides of the wavy-line pattern of the circular bodies that are adjacent are connected by way of the coiled elements,
wherein a knob portion is formed at each apex of the wavy-line pattern of the circular bodies, the knob portion including an extension portion extending in the axis direction having a width greater than a width of the coiled elements and a tip portion formed at a tip of the extension portion,
wherein the coiled element is connected with the knob portion,
wherein a slit is formed at a part of the extension portion of the knob portion, the slit extending in the axis direction from an inner peripheral portion at the apex of the wavy-line pattern of the circular body,
wherein opposite side edges of the slit are linear, extending in parallel,
wherein the tip portion is a semicircle portion of semicircular shape,
wherein the coiled element has a curve portion at both ends thereof and the coiled element is connected with the circular body via the curve portion,
wherein the curve portion is formed so that a tangential direction of the curve portion at a connecting end at which the coiled element connects with the circular body coincides with the axis direction, and
wherein a connecting end at which the apex located at one side in the axis direction of the wavy-line pattern of the circular body connects with the coiled element and a connecting end at which the apex located at the other side in the axis direction of the wavy-line pattern of the circular body connects with the coiled element are offset from the center of the apex to opposite sides in a circumferential direction.

2. The highly flexible stent according to claim 1, wherein the extension portion extends linearly in the axis direction.

3. The highly flexible stent according to claim 1, wherein the highly flexible stent is formed from a super elastic alloy.

4. The highly flexible stent according to claim 3, wherein the super elastic alloy is a nickel titanium alloy.

5. The highly flexible stent according to claim 1, wherein the highly flexible stent is a stent to be placed in a cerebral blood vessel.

* * * * *